United States Patent
Trahey et al.

(10) Patent No.: US 6,764,448 B2
(45) Date of Patent: Jul. 20, 2004

(54) METHODS, SYSTEMS, AND COMPUTER PROGRAM PRODUCTS FOR IMAGING USING VIRTUAL EXTENDED SHEAR WAVE SOURCES

(75) Inventors: Gregg E. Trahey, Hillsborough, NC (US); Kathryn R. Nightingale, Durham, NC (US); Roger W. Nightingale, Durham, NC (US); Stephen McAleavey, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 10/266,096

(22) Filed: Oct. 7, 2002

(65) Prior Publication Data

US 2004/0068184 A1 Apr. 8, 2004

(51) Int. Cl.[7] ................................................. A61B 8/00
(52) U.S. Cl. ...................................................... 600/437
(58) Field of Search ................................ 600/437–471; 128/916; 73/620–633; 367/7, 11, 130, 138

(56) References Cited

U.S. PATENT DOCUMENTS

| | | | |
|---|---|---|---|
| 4,694,434 A | 9/1987 | von Ramm et al. | 367/7 |
| 5,487,387 A | 1/1996 | Trahey et al. | 128/660.02 |
| 5,546,807 A | 8/1996 | Oxaal et al. | 73/606 |
| 5,606,971 A | 3/1997 | Sarvazyan | 128/660.02 |
| 5,810,731 A | 9/1998 | Sarvazyan | 600/438 |
| 5,921,928 A | 7/1999 | Greenleaf et al. | 600/437 |
| 6,371,912 B1 | 4/2002 | Nightingale et al. | 600/437 |
| 2002/0010398 A1 * | 1/2002 | Bonnefous | 600/442 |

OTHER PUBLICATIONS

Dresner et al.; "Magnetic Resonance Elastography of Skeletal Muscle" *Journal of Magnetic Resonance Imaging* 13 269–276 (2001).

Lerner et al.; ""Sonoelasticity" Images Derived From Ultrasound Signals In Mechanically Vibrated Tissues" *Ultrasound in Med. & Biol.* 16:3 231–239 (1990).

Levinson et al.; "Soloelastic Determination Of Human Skeletal Muscle Elasticity" *J. Biomechanics* 28:10 1145–1154 (1995).

Nightingale et al.; "A Finite Element Model of Remote Palpation of Breast Lesions Using Radiation Force: Factors Affecting Tissue Displacement" *Ultrasonic Imaging* 22 35–54 (2000).

Nightingale et al.; "On the feasibility of remote palpation using acoustic radiation force" *J. Acoust. Soc. Am.* 110:1 625–634 (2001).

Nightingale et al.; "Acoustic Radiation Force Impulse Imaging: Ex Vivo And In Vivo Demonstration Of Transient Shear Wave Propagation" *Proceedings of ISBI* Duke University Departments of Biomedical Engineering and Pathology (2002).

Nightingale et al.; "Acoustic Radiation Force Impulse Imaging: Remote Palpation Of The Mechanical Properties Of Tissue" *Proceedings of Ultrasonics Symposium (IEEE UFFC)* Duke University (2002).

(List continued on next page.)

Primary Examiner—Ali Imam
(74) Attorney, Agent, or Firm—Myers Bigel Sibley & Sajovec

(57) ABSTRACT

Ultrasound energy is transmitted into tissue in a first direction to provide a virtual extended shear wave source. The virtual extended shear wave source generates an extended shear wave that propagates in a second direction substantially orthogonal to the first direction to cause movement in the first direction of tissue that is offset from the virtual extended shear wave source in the second direction. Related ultrasound imaging systems and computer program products are also disclosed.

35 Claims, 5 Drawing Sheets

OTHER PUBLICATIONS

Parker et al.; "Tissue Response To Mechanical Vibration For Sonoelasticity Imaging" *Ultrasound in Med. & Biol.* 16:3 241–246 (1990).

Sarvazyan et al.; "Shear Wave Elasticity Imaging: A New Ultrasonic Technology of Medical Diagnostics" *Ultrasound in Med. & Biol.* 24:9 1419–1435 (1998).

Taylor et al.; "Three–dimensional sonoelastography: principles and practices" *Phys. Med. Biol.* 45 1477–1494 (2000).

Wu et al.; "MR Imaging of Shear Waves Generated by Focused Ultrasound" *Magnetic Resonance in Medicine* 43 111–115 (2000).

* cited by examiner

METHODS, SYSTEMS, AND COMPUTER PROGRAM PRODUCTS FOR IMAGING USING VIRTUAL EXTENDED SHEAR WAVE SOURCES

STATEMENT OF GOVERNMENT SUPPORT

This invention was made with Government support under Grant No. RG-00-0272 from the Whitaker Foundation and and under Federal Grant No. 1R01CA92183-01 from the National Institutes of Health, National Cancer Institute. The Government has certain rights to this invention.

FIELD OF THE INVENTION

The present invention relates to the field of imaging in general, and more particularly, to the field of ultrasound imaging.

BACKGROUND

It is known to use imaging methods to investigate the mechanical properties of tissues. In particular, it is known to evaluate the mechanical properties of tissue using shear wave characteristics of the tissue. For example, some of the tissue properties which can be examined using shear waves include the speed at which shear waves travel in the tissue, the attenuation that the shear waves exhibit while propagating in the tissue, and the associated wavelengths of the shear waves.

As discussed in A. Sarvazyan et al. entitled "Shear wave elasticity imaging: A new ultrasonic technology of medical diagnostics," *Ultrasound Med. Biol.,* 24(9):1419–1435, 1998 (hereinafter "Sarvazyan"), shear waves are generated by focussing low frequency ultrasound waves on a focal point to provide point shear wave sources. These types of shear waves are also discussed, for example, in U.S. Pat. No. 5,810,731 to Sarvazyan et al. entitled Method and Apparatus for Elasticity Imaging Using Remotely Induced Shear Wave.

SUMMARY

Embodiments according to the present invention can provide methods, systems and computer program products for imaging using virtual extended shear wave sources. Pursuant to these embodiments, ultrasound energy can be transmitted into tissue in a first direction to provide a virtual extended shear wave source. The virtual extended shear wave source can generate an extended shear wave that propagates in a second direction substantially orthogonal to the first direction to cause movement in the first direction of tissue that is offset from the virtual extended shear wave source in the second direction.

The movement (or displacement) of the tissue caused by the extended shear wave can be used to determine properties or images of the tissue. For example, in some embodiments according to the present invention, the displacements can be used to generate images of mean shear wave velocity, images of mean shear wave attenuation, images of differences in shear wave velocities and attenuations as a function of extended shear waves propagating in different directions or angles through the tissue, images of mean shear wave wavelength, images of differences in shear wave wavelength, and the to like.

In some embodiments according to the present invention, the ultrasound energy is transmitted by an ultrasound transducer array having an associated focal point, wherein the extended shear wave is located on at least one of a far side and a near side of the focal point relative to the ultrasound transducer array.

In some embodiments according to the present invention, the virtual extended shear wave source can be a transmit ultrasound beam having an amplitude sufficient to generate a trackable extended shear wave. In some embodiments according to the present invention, the transmitted ultrasound energy causes the tissue along the first direction to displace in a range between about 0.1 $\mu$m and about 300 $\mu$m.

In some embodiments according to the present invention, the virtual extended shear wave source can have an associated frequency in a range between about 1 MHz and about 25 MHz.

In some embodiments according to the present invention, transmitting can include transmitting ultrasound energy from an ultrasound transducer array having an associated focal point, wherein a portion of the virtual extended shear wave source extends at least a portion of a distance between the ultrasound transducer array and the focal point.

In some embodiments according to the present invention, the transmitting can include transmitting first ultrasound energy in the first direction to provide a first virtual extended shear wave source that generates a first extended shear wave. Furthermore, second ultrasound energy can be transmitted into the tissue in a third direction to provide a second virtual extended shear wave source, wherein the second virtual extended shear wave source generates a second extended shear wave that propagates substantially orthogonal to the third direction to cause movement in the third direction of tissue that is offset from the second virtual extended shear wave source.

In some embodiments according to the present invention, the virtual extended shear wave can be a first virtual extended shear wave and the transmitted ultrasound energy can be steered into the tissue in a third direction of transmission, that is different than the first, to provide a second virtual extended shear wave source in the tissue.

In some embodiments according to the present invention, a sub-aperture of an ultrasound transducer array used to transmit the ultrasound energy can be changed to provide a second virtual extended shear wave source in the tissue in a third direction.

In some embodiments according to the present invention, the steering can be provided by applying a phased excitation to an ultrasound transducer to steer the transmitted ultrasound energy in the third direction.

In some embodiments according to the present invention, the tracking can be provided by tracking the movement of the offset tissue in response to the extended shear wave using receive mode parallel processing. In some embodiments according to the present invention, the movement of the offset tissue in response to the extended shear wave can be tracked using a second modality.

In some embodiments according to the present invention, tissue can be tracked to obtain first position data associated with tissue. Ultrasound energy can be transmitted into the tissue in a first direction to provide a virtual extended shear wave source that generates an extended shear wave that propagates in a second direction substantially orthogonal to the first direction to cause movement in the first direction of tissue that is offset from the virtual extended shear wave source in the second direction. The offset tissue can be tracked to obtain second position data. A displacement map can be determined based on the first and second position data and an image of the tissue can be generated based on the displacement map.

DESCRIPTION OF EMBODIMENTS ACCORDING TO THE INVENTION

Figure 1:
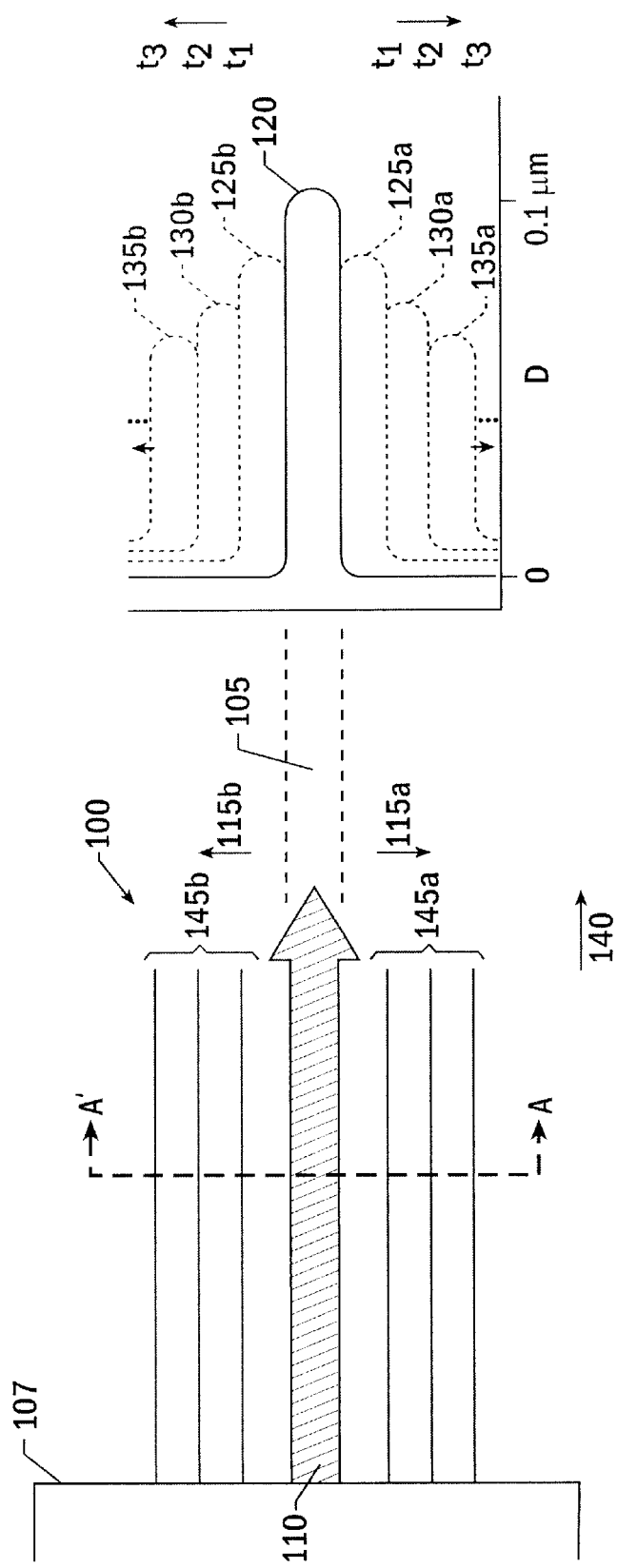
FIG. 1 is a schematic diagram that illustrates virtual extended shear wave sources and associated extended shear waves according to embodiments of the present invention.

The present invention now will be described more fully hereinafter with reference to the accompanying drawings, in which typical embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the relative sizes of regions may be exaggerated for clarity.

As will be appreciated by one of skill in the art, the present invention may be embodied as a method, data processing system or computer program product. Accordingly, the present invention may take the form of an entirely hardware embodiment, an entirely software-embodiment or an embodiment combining software and hardware aspects. Furthermore, the present invention may take the form of a computer program product on a computer-readable storage medium having computer-readable program code means embodied in the medium. Any suitable computer readable medium may be utilized including hard disks, CD-ROMs, optical storage devices, or magnetic storage devices.

The present invention is also described herein using a flowchart illustration. It will be understood that each block of the flowchart illustration, and combinations of blocks in the flowchart illustration, can be implemented by computer program instructions. These computer program instructions may be loaded onto a computer or other programmable apparatus to produce a machine, such that the instructions which execute on the computer or other programmable apparatus create means for implementing the functions specified in the flowchart block or blocks.

These computer program instructions may also be stored in a computer-readable memory that can direct a computer or other programmable apparatus to function in a particular manner, such that the instructions stored in the computer-readable memory produce an article of manufacture including instruction means which implement the function specified in the flowchart block or blocks. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Accordingly, blocks of the flowchart illustration support combinations of means for performing the specified functions and combinations of steps for performing the specified functions. It will also be understood that each block of the flowchart illustration, and combinations of blocks in the flowchart illustration, can be implemented by special purpose hardware-based computer systems which perform the specified functions or steps, or combinations of special purpose hardware and computer instructions.

Embodiments according to the present invention are described herein with reference to the term "tissue." It will be understood that the term tissue can include biological materials, such as, blood, organs, vessels, and other biological objects found in a body. It will be further understood that embodiments according to the present invention may be applicable to humans as well as other species. Embodiments according to the present invention may also be utilized to image objects other than tissue.

It will be understood that the scope of the present invention includes, for example, two dimensional (2D) ultrasound imaging and 3D (or volumetric) ultrasound imaging. In addition, the components of the ultrasound imaging described herein may be packaged as a single unit or packaged separately and interconnected to provide the functions described herein.

Embodiments according to the present invention are also described by reference to Acoustic Radiation Force (ARF) which is described in greater detail, for example, in U.S. Pat. No. 6,371,912, entitled Method and Apparatus for the Identification and Characterization of Regions of Increased Stiffness to Nightingale, et al., filed Sep. 18, 2000, the entire disclosure of which is incorporated herein by reference. In brief, ARF can be used to apply a force to tissue thereby causing the tissue to move in the direction of the force.

FIG. 1 is a block diagram that illustrates the generation of extended shear waves according to embodiments of the present invention. In particular, an excitation is applied to an ultrasound transducer 107 to transmit ultrasound energy in a direction 140 to provide a virtual extended shear wave source 110 that extends into the tissue. As discussed above, in some embodiments according to the present invention, the virtual extended shear wave source 110 is generated by ARF. In some embodiments according to the present invention, the ultrasound energy used to provide the virtual extended shear wave source 110 has an associated frequency in a range between about 1 MHz and about 25 MHz and preferably in a range between about 5 MHz and about 25 MHz.

As used herein, the term "virtual" extended shear wave source includes ultrasound energy that is transmitted by an ultrasound transducer which can provide the virtual extended shear wave sources remote from the transducer as shown, for example, in FIG. 1. In some embodiments according to the present invention, the virtual extended shear wave source can extend from the transducer in the direction 140 by a distance in a range between about 0.2 $\mu$m and about 8.0 cm. In other embodiments according to the present invention, the virtual extended shear wave sources can extend other distances.

The virtual extended shear wave source 110 causes a displacement in a region 105 of the tissue 100 in the direction 140 which generates a first extended shear wave 145a that propagates in a direction 115a that is substantially orthogonal to the direction 140. The virtual extended shear wave source 110 also generates a second extended shear wave 145b which propagates in a direction 115b which is opposite the direction 115a and substantially orthogonal to the direction 140. It will be understood that, although not shown, multiple extended shear waves can be generated by providing additional virtual extended shear wave sources 110 by, for example, exciting the ultrasound transducer 107 again.

As shown in FIG. 1, the extended shear waves 145a,b propagate outwardly from the virtual extended shear wave source 110 over time. In some embodiments according to the present invention, as shown in the right hand portion of FIG.

1 that depicts the displacement of tissue at cross-section A–A', the virtual extended shear wave source 110 causes a displacement 120 of the tissue sufficient so as to be "trackable" by an ultrasound imaging system. In some embodiments according to the present invention, the displacement caused by the virtual extended shear wave source 110 is in a range between about 0.1 µm and about 300 µm. Other displacements can be provided.

As the extended shear waves 145a,b propagate outward over time, the extended shear waves 145a,b generate corresponding displacements 125a,b; 130a,b; and 135a,b in the tissue 100 over time. For example, as shown in FIG. 1, at time t1 the extended shear waves 145a,b cause tissue that is offset from the region 105 to move displacements 125a,b below and above the region 105. At a time t2 the propagation of the extended shear waves 145a,b causes tissue that is further offset from the region 105 to move displacements 130a,b. At a time t3, the further propagation of the extended shear waves 145 causes the tissue farther offset from the region 105 to move displacements 135a,b. Although FIG. 1 shows the extended shear wave propagating outward at only three times (t1, t2, and t3) it will be understood that the extended shear wave continues to propagate outwardly over time (as denoted by the ellipsis). It will be further understood that the extended shear waves may propagate in a continuous manner through the tissue.

The displacement of the tissue caused by the extended shear waves can be used to determine properties or images of the tissue. For example, in some embodiments according to the present invention, the displacements can be used to generate images of mean shear wave velocity, images of mean shear wave attenuation, images of differences in shear wave velocities and attenuations as a function of extended shear waves propagating in different directions or angles through the tissue, images of mean shear wave wavelength, images of differences in shear wave wavelength, and the like.

Figure 2:
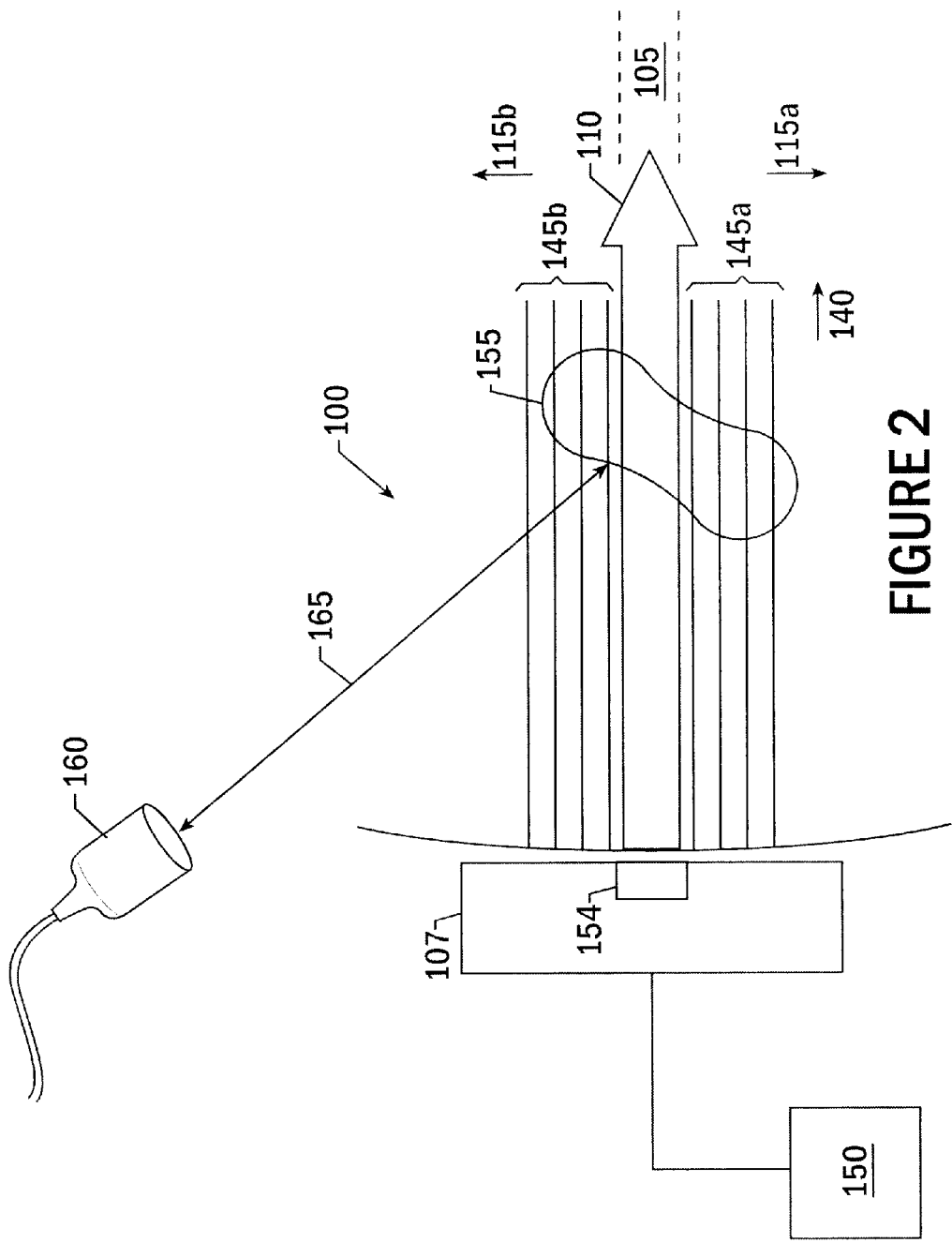
FIGS. 2–5 are block diagrams that illustrate ultrasound imaging methods, systems, and computer program products according to embodiments of the present invention.

FIG. 2 is a block diagram that illustrates embodiments of ultrasound methods, systems, and computer program products according to the present invention. As shown in FIG. 2, the ultrasound transducer array 107 is connected to an ultrasound system 150. In some embodiments according to the present invention, the ultrasound transducer array 107 is a linear array or a two dimensional (2D) array that can have phased excitations applied thereto to steer ultrasound energy generated by the ultrasound transducer array 107. In some embodiments according to the present invention, the ultrasound system 150 is a B mode scanner that provides tomographic images of the tissue scanned. In some embodiments according to the present invention, the ultrasound system 150 is a real time three dimensional ultrasound scanner as described, for example, in U.S. Pat. No. 5,546,807 to Oxaal et al. entitled High Speed Volumetric Ultrasound Imaging System, the entire disclosure of which is incorporated herein by reference.

The ultrasound system 150 can include a processor that can be programmed to provide various excitations to the ultrasound transducer array 107. In particular, the ultrasound system 150 can be programmed to excite selected transducer elements 154 that define a sub-aperture within the ultrasound transducer array 107 that can generate ultrasound energy to provide the virtual extended shear wave source 110. For example, the selected ultrasound transducer elements 154 can define a sub-aperture within the ultrasound transducer array 107 which includes 20 ultrasound transducer elements. The selected ultrasound transducer elements 154 can be excited with, for example, a series of excitations within a square wave envelope to provide the virtual extended shear wave source 110. In some embodiments according to the present invention, other types of envelopes, such as a cosine envelope or a Blackman envelope, can be used.

As discussed above in reference to FIG. 1, the virtual extended shear wave source 110 generates extended shear waves 145a,b which propagate in opposite directions 115a,b outwardly from the virtual extended shear wave source 110 to cause movement of tissue, such as that found in object 155, in the direction 140. It will be understood that the tissue also moves in a direction that is opposite to the direction 140 when the ultrasound energy used to provide the virtual extended shear wave source 110 is removed, thereby causing the displaced tissue to return to its original position. It will further be understood that the tissue that is offset, for example, from the region 105 will also return to the respective original positions over time.

The rate at which the displaced tissue returns to its original position may be used to determine properties of the tissue. For example, muscle may exhibit greater stiffness than fat tissue and, therefore, may be distinguished based on the rate at which the displaced tissue returns to the original position. Moreover, some tissue may exhibit different velocity, attenuation, or stiffness in different directions. In particular, different tissues may have different mechanical properties when observed from different directions (anisotropy). For example, muscle may exhibit greater stiffness in the direction of the muscle fibers than crosswise to the fibers.

The displacement of tissue 100 can be tracked using tracking 165 provided by an imaging modality 160 according to techniques that are well known by those having skill in the art. As used herein, the term "tracking" includes receiving reflected ultrasound energy from the tissue which can be performed using techniques known to those skilled in the art.

In some embodiments according to the present invention, receive mode parallel processing can be used to track the displacement of tissue. Receive mode parallel processing is described, for example, in U.S. Pat. No. 4,694,434 to von Ramm and Smith which disclosed a steered array acoustic imaging scanner capable of producing a high-speed pyramidal scan to obtain a volumetric three-dimensional image using a two-dimensional array transducer and receive mode parallel processing, the entire disclosure of which is hereby incorporated herein by reference. In other embodiments according to the present invention, other types of tracking can be used.

In some embodiments according to the present invention, the imaging modality 160 is a second ultrasound system. In other embodiments according to the present invention, the imaging modality 160 is MRI, CT, or the like. It will be further understood that the ultrasound transducer 107 can be used to perform the tracking 165. In such embodiments, the ultrasound transducer 107 can be used to generate the virtual extended shear wave source 110 and, later, can be used to track the movement of the tissue 100 caused by the propagation of the extended shear waves.

Figure 3:
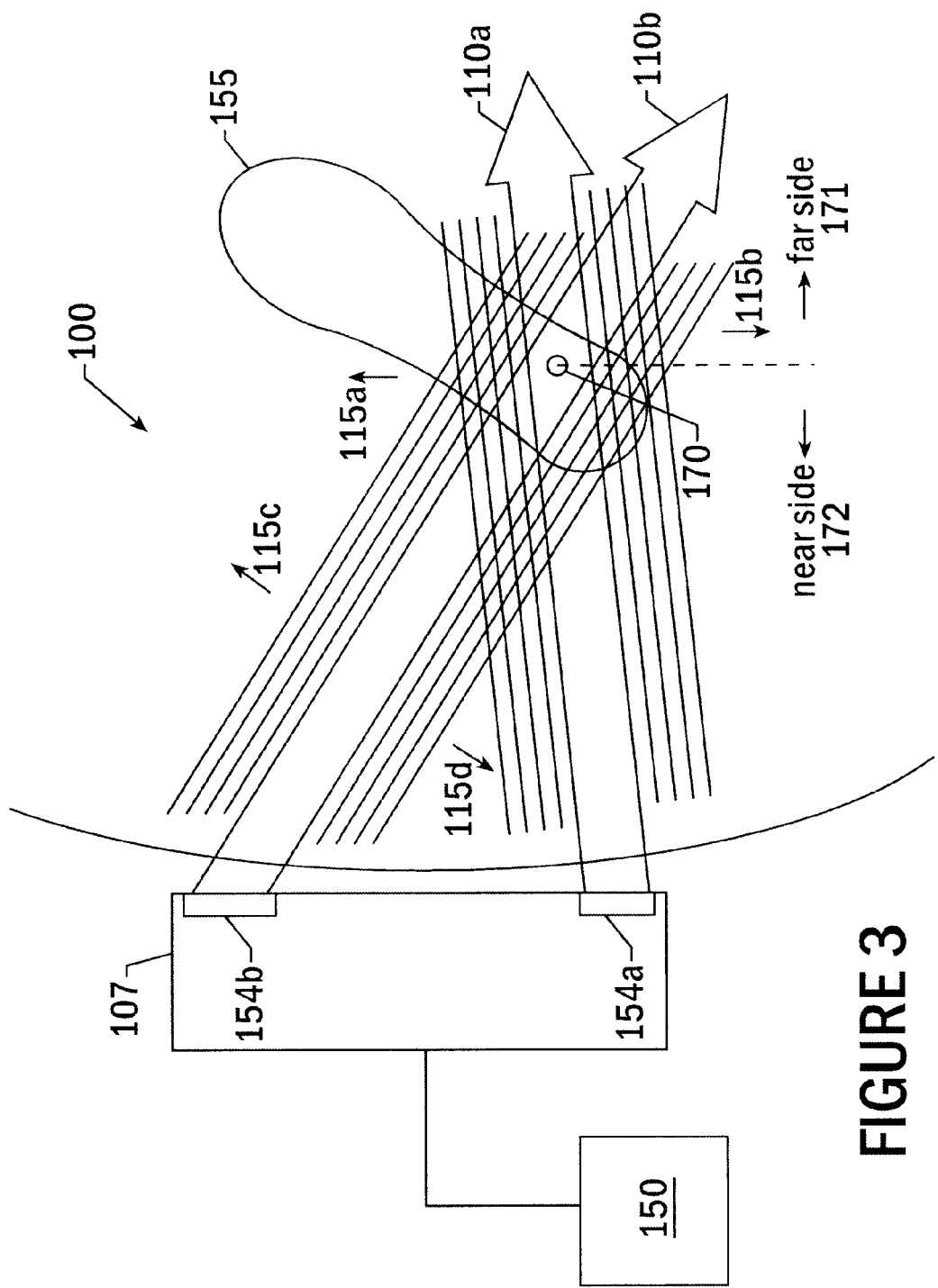

FIG. 3 is a block diagram that illustrates embodiments of ultrasound methods, systems, and computer program products according to the present invention. As shown in FIG. 3, first and second sub-apertures 154a,b are defined within the ultrasound transducer array 107, which provide the virtual extended shear wave sources 110a,b respectively, which propagate in the tissue 100 as shown. The first and second sub-apertures 154a,b are used to steer the virtual extended shear wave sources 110a,b towards a focal point 170 in the tissue 100.

The virtual extended shear wave source 110a generates extended shear waves that propagate outwardly from the virtual extended shear wave source 110a in the directions 115a,b. The virtual extended shear wave source 110b generates extended shear waves that propagate outwardly from the virtual extended shear wave source 110b in the directions 115c,d. In some embodiments according to the present invention, the extended shear waves are located on at least one of a far side 171 of the focal point 170 and a near side 172 of the focal point 170.

In operation, the ultrasound system 150 can be used to alternate between providing the first and second virtual extended shear waves 110a,b. For example, in some embodiments according to the present invention, the ultrasound system 150 may use the first sub-aperture 154a to provide the first virtual extended shear wave source 110a to thereby generate the respective extended shear waves which can be tracked by the ultrasound system 150. The ultrasound system 150 may then use the second sub-aperture 154b to provide the second virtual extended shear wave source 110b to thereby generate the respective virtual extended shear waves which are also tracked.

Steering the virtual extended shear wave sources 110a,b can provide displacement data for shear waves propagating in different directions through the object 155 to thereby determine properties of the tissue based on the different effects of shear waves that propagate through the object 155 in different directions. As discussed above, different tissues may be discriminated based on the existence and degree of differences in their respective anisotropic properties. Therefore, the ability to steer the extended shear waves through the object 155 at different angles may allow tissue anisotropy properties to be determined.

Figure 4:
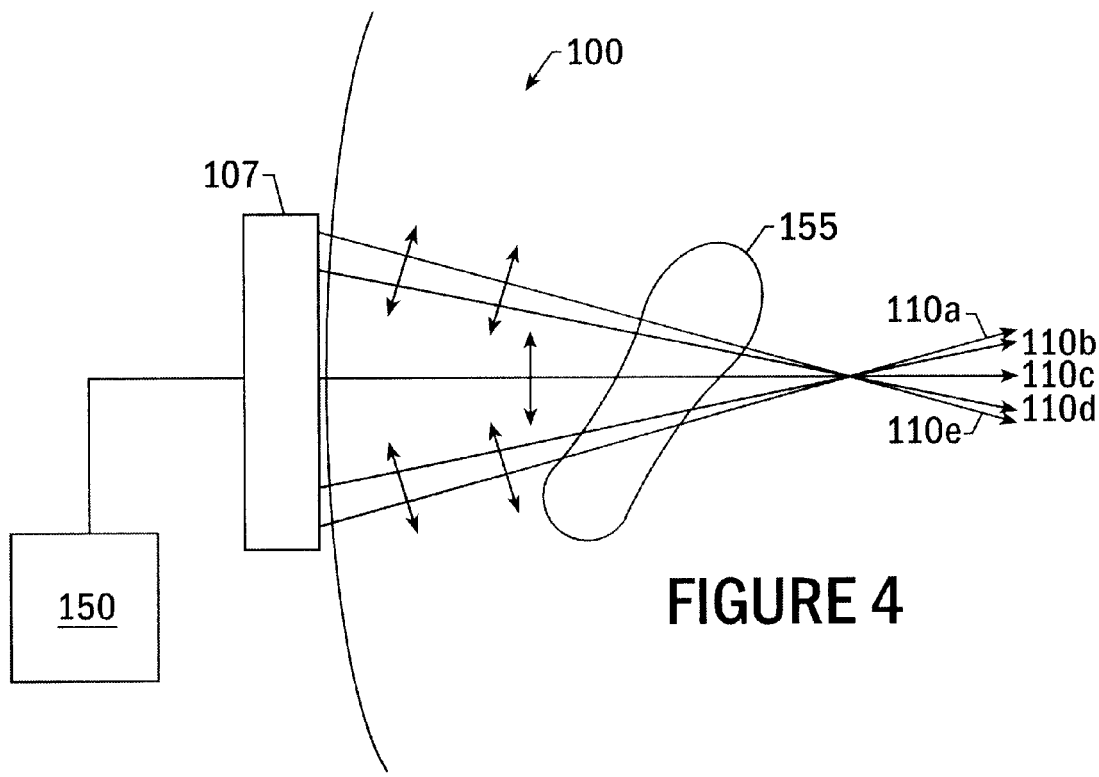

FIG. 4 is a block diagram that schematically illustrates embodiments of ultrasound imaging methods, systems, and computer program products according to the present invention. In particular, FIG. 4 shows an increased number of virtual extended shear wave sources 110a–e, each generating associated extended shear waves, which are steered by a respective plurality of sub-apertures within the ultrasound transducer array 107. The ultrasound transducer array 107 shown in FIG. 4 is also focused beyond the tissue 155. Such focusing can provide additional ultrasound energy at the focal point which can increase the depth to which images of the tissue can be provided. It will also be understood that the array 107 can also be focused on other areas and the virtual extended shear wave sources 110 can be steered in different directions than those shown. It will also be understood that the first and second virtual extended shear wave sources can be generated substantially simultaneously or at different times.

Figure 5:
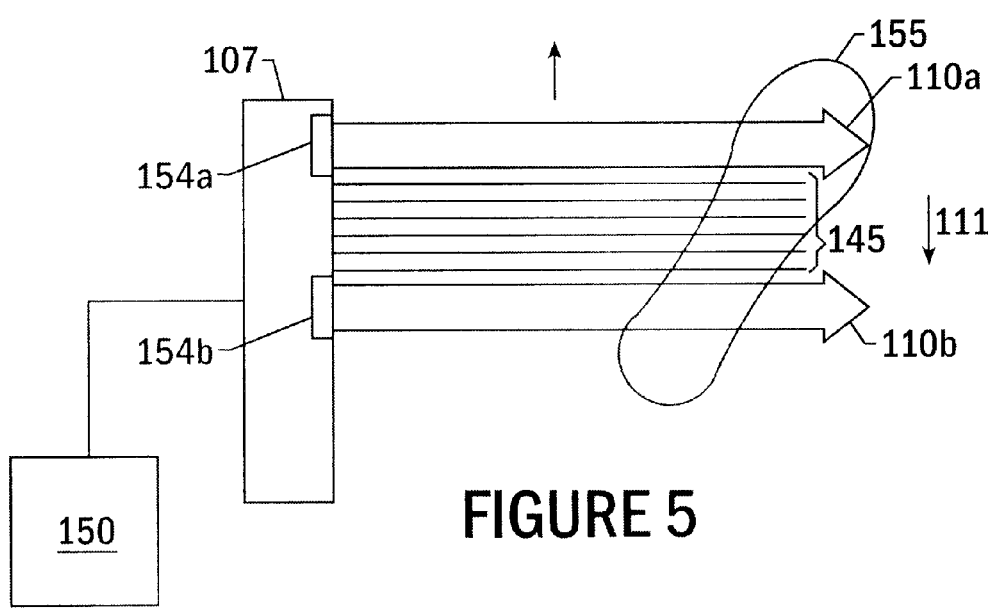

FIG. 5 is a block diagram that illustrates embodiments of ultrasound imaging methods, systems, and computer program products according to the present invention. The ultrasound system 150 can operate so as to unfocus the sub-apertures 154a,b and steer the first and second virtual extended shear wave sources 110a,b in a forward direction. In particular, the ultrasound system 150 can be programmed to use a first sub-aperture 154a of the ultrasound transducer 107 to provide a first virtual extended shear wave source 110a that, in turn, generates an extended shear wave 145 which propagates in a direction 111. Although FIG. 5 illustrates the extended shear wave 145 propagating in only one direction, it will be understood that an extended shear wave can also propagate in a direction opposite to the direction 111 and is omitted for the sake of clarity.

The ultrasound system 150 can use a second sub-aperture 154b to provide the second virtual extended shear wave source 110b at a time t at which it is predicted that the shear wave 145 will have reached the location within the tissue 155 in which the second virtual extended shear wave source 110b is to be provided. For example, if the shear wave 145 is predicted to propagate from the first virtual extended shear wave source 110a to a location in the tissue 155 opposite the second sub-aperture 154b in t1 seconds, the ultrasound imaging system 150 can be programmed to excite the second sub-aperture 154b at a time which will generate the second extended shear wave to spatially coincide with the first extended shear waves 145. Therefore, the second sub-aperture 154b can be excited a predetermined time after the first sub-aperture 154a is excited so that the first and second extended shear waves add constructively and provide increased amplitude to the extended shear wave 145 as it propagates through the tissue. It will be understood that the first and second virtual extended shear wave sources can be generated substantially simultaneously or at different times.

Figure 6:
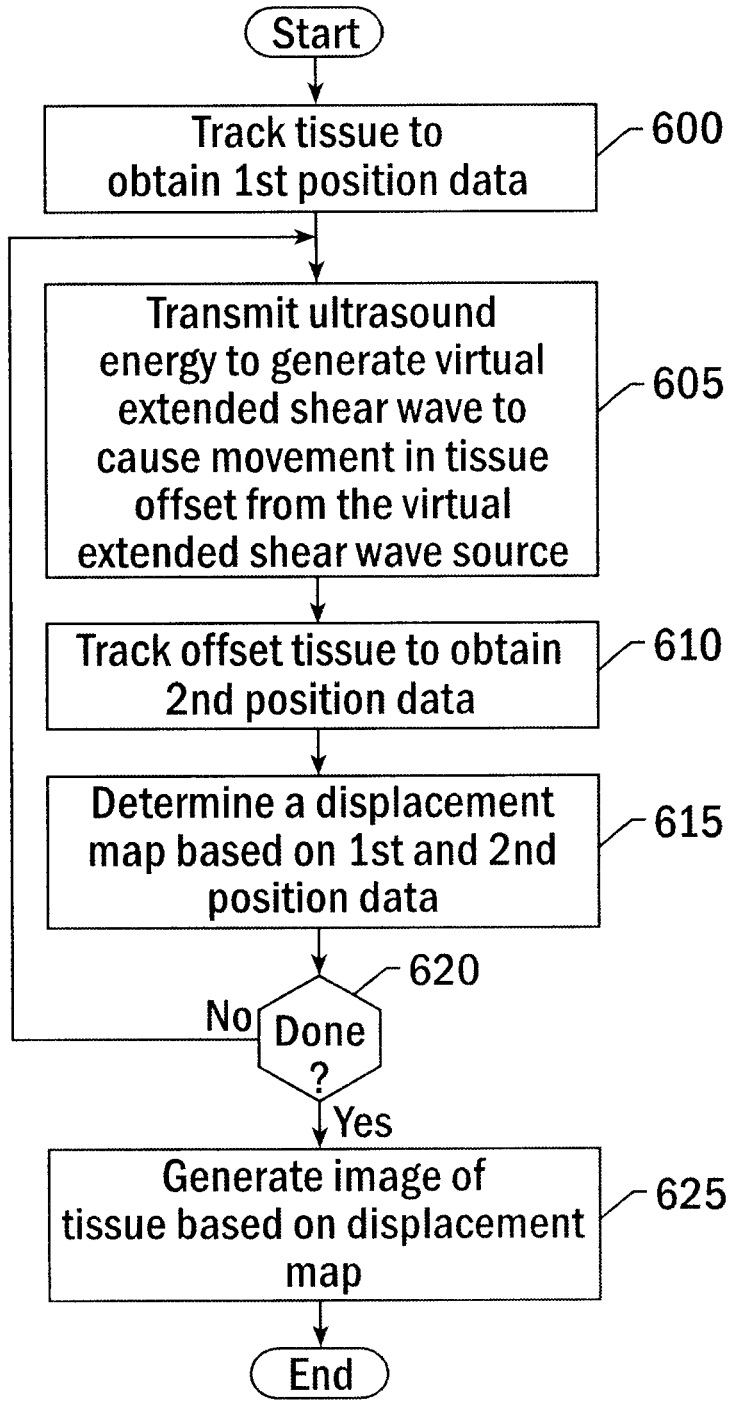
FIG. 6 is a flowchart that illustrates operations of imaging methods, systems, and computer program products according to embodiments of the present invention.

FIG. 6 is a flowchart that illustrates operations of ultrasound imaging methods, systems, and computer program products according to embodiments of the present invention. In operation, an imaging modality is used to track tissue to be examined to obtain initial position data for the tissue (block 600). The ultrasound transducer is used to transmit ultrasound energy into the tissue to provide a virtual extended shear wave source that generates a virtual extended shear wave that causes movement of the tissue that is offset from the virtual extended shear wave source (block 605). The movement of the tissue caused by the extended shear wave is tracked to obtain displacement data (block 610).

A displacement map is determined based on the initial position and the displacement data (block 615). It will be understood that the displacement map can be determined using techniques known to those skilled in the art. For example, in some embodiments according to the present invention, motion tracking techniques can be used to determine differences between the initial and displaced locations of the tissue. In some embodiments according to the present invention, techniques such as cross-correlation and sum-absolute-difference are used to determine a series of 2D displacement maps over time that quantify the displacement of the tissue.

If further imaging of the tissue is to be conducted (block 620), the direction of the virtual extended share wave source can be changed (block 617) using, for example, beam steering to generate a new extended shear wave from a new direction through the tissue (block 605) and the resulting displacement of tissue in the new direction can be tracked. The resulting displacement of the tissue can be used to determine additional displacement maps. If however, no further investigation of the tissue is to be conducted (block 620), image(s) of the tissue can be generated based on the determined displacement maps (block 625).

The displacement maps can be used to determine shear wave velocity using tomographic reconstruction techniques. Tomographic images of a material property may be achieved through direct methods such as filtered backprojection, Fourier transformation, or using iterative reconstruction methods such as an algebraic reconstruction approach as discussed in Herman, Image Reconstruction from Projections.

The number of directions from which the tissue may be interrogated may lead to a multiplicity of values for a tissue property at a particular point. Values for the property may be determined using techniques known to those skilled in the art, such as, a least-square technique, a pseudoinverse technique, or a Bayesian technique. Other approaches or a combination of approaches can also be used for solutions.

Measurements of anisotropic properties can be used to provide a vector description of each point in the image, wherein each vector component describes the response to an extended shear wave made from a particular direction. Features of the vector descriptions may be extracted using techniques known to those skilled in the art, such as, a Hotelling transform, a Karhunen-Loeve expansion, or a Bayes classifier, as discussed for example, in Gonzales and Woods, Digital Image Processing, to reduce the volume of data.

In the drawings and specification, there have been disclosed embodiments of the invention and, although specific terms are employed, they are used in a generic and descriptive sense only and not for purposes of limitation, the scope of the invention being set forth in the following claims.

What is claimed:

1. A method of scanning tissue, the method comprising transmitting ultrasound energy into tissue in a first direction to provide a virtual extended shear wave source that generates an extended shear wave that propagates in a second direction substantially orthogonal to the first direction to cause movement in the first direction of tissue that is offset from the virtual extended shear wave source in the second direction.

2. A method according to claim 1 further comprising: tracking the movement of the offset tissue in response to the extended shear wave.

3. A method according to claim 2 further comprising: determining a displacement map including displacement values associated with respective portions of the tissue subject to the extended shear wave based on the tracking.

4. A method according to claim 3 wherein the transmitting is preceded by imaging the tissue to determine initial locations of the tissue prior to generation of the extended shear wave in the tissue; and
wherein the determining comprises determining the displacement map based on the initial locations and the tracking.

5. A method according to claim 4 further comprising: generating an image of the offset tissue based on the determined displacement map.

6. A method according to claim 2 wherein the tracking comprises tracking the movement of the offset tissue in response to the extended shear wave using receive mode parallel processing.

7. A method according to claim 1 wherein the ultrasound energy is transmitted by an ultrasound transducer array having an associated focal point, wherein the extended shear wave is located on at least one of a far side and a near side of the focal point relative to the ultrasound transducer array.

8. A method according to claim 1 wherein the virtual extended shear wave source comprises a transmit ultrasound beam having an amplitude sufficient to generate a trackable extended shear wave.

9. A method according to claim 1 wherein the virtual extended shear wave source has an associated frequency in a range between about 1 MHz and about 25 MHz.

10. A method according to claim 1 wherein transmitting comprises transmitting ultrasound energy from an ultrasound transducer array having an associated focal point, wherein a portion of the virtual extended shear wave source extends at least a portion of a distance between the ultrasound transducer array and the focal point.

11. A method according to claim 1 wherein transmitting comprises transmitting first ultrasound energy in the first direction to provide a first virtual extended shear wave source that generates a first extended shear wave, the method further comprising:
transmitting second ultrasound energy into the tissue in a third direction to provide a second virtual extended shear wave source, wherein the second virtual extended shear wave source generates a second extended shear wave that propagates substantially orthogonal to the third direction to cause movement in the third direction of tissue that is offset from the second virtual extended shear wave source.

12. A method according to claim 11 wherein transmitting the first and second ultrasound energy into the tissue comprises transmitting the first and second ultrasound energy into the tissue substantially simultaneously.

13. A method according to claim 12 wherein the first and second virtual extended shear wave sources intersect one another in the tissue.

14. A method according to claim 12 wherein the first and second virtual extended shear wave sources do not intersect one another in the tissue.

15. A method according to claim 1 wherein a length of the virtual extended shear wave source is in a range between about 0.2 mm and about 8.0 cm.

16. A method according to claim 1 wherein the virtual extended shear wave source further generates a second extended shear wave that propagates opposite the second direction.

17. A method according to claim 1 wherein the transmitted ultrasound energy causes the tissue along the first direction to displace in a range between about 0.1 $\mu$m and about 300 $\mu$m.

18. A method of imaging tissue using shear wave ultrasound, the method comprising:
tracking tissue to obtain first position data associated with tissue;
transmitting ultrasound energy into the tissue in a first direction to provide a virtual extended shear wave source that generates an extended shear wave that propagates in a second direction substantially orthogonal to the first direction to cause movement of tissue that is offset from the virtual extended shear wave source;
determining at least one imaging parameter based on at least the first position data; and
generating image data associated with the tissue based on the at least one imaging parameter.

19. A method according to claim 18 further comprising: tracking the offset tissue in response to the extended shear wave to obtain second position data using receive mode parallel processing.

20. A method according to claim 18 wherein the at least one imaging parameter is selected from the group consisting of a displacement parameter, an elasticity parameter, and a mechanical property parameter.

21. A method according to claim 19 wherein the determining comprises determining the at least one imaging parameter based on the first and second position data.

22. A method according to claim 19 wherein the determining comprises determining a displacement map based on the first and second position data.

23. A method according to claim 19 wherein the virtual extended shear wave source comprises a first source that generates a first extended shear wave and the image data comprises first image data, the method further comprising:

transmitting ultrasound energy in a third direction to provide a second source that generates a second extended shear wave that propagates substantially orthogonal to the third direction to cause movement of tissue that is offset from the second source, the third direction being different than the first direction; and tracking the second extended shear wave to obtain third position data;

determining a second imaging parameter based on the third position data; and generating second image data associated with the tissue based on the second imaging parameter.

24. A method according to claim 18 wherein the virtual extended shear wave source has an associated frequency in a range between about 1 MHz and about 25 MHz.

25. A method according to claim 18 wherein transmitting comprises transmitting ultrasound energy from an ultrasound transducer array having an associated focal point, wherein a portion of the virtual extended shear wave source extends at least a portion of a distance between the ultrasound transducer array and the focal point.

26. A method according to claim 18 wherein transmitting comprises transmitting first ultrasound energy in the first direction to provide a first source that generates a first extended shear wave, the method further comprising:

transmitting ultrasound energy into the tissue in a third direction to provide a second source, wherein the second source generates a second extended shear wave that propagates substantially orthogonal to the third direction to cause movement of tissue that is offset from the second source.

27. A method according to claim 19 wherein the determining comprises determining a displacement map including displacement values associated with respective portions of the tissue subject to the extended shear wave based on the tracking.

28. A method according to claim 27 wherein the transmitting is preceded by imaging the tissue to determine initial locations of the tissue prior to generation of the extended shear wave in the tissue; and wherein the determining comprises determining the displacement map based on the initial locations and the tracking.

29. A method according to claim 18 wherein a length of the virtual extended shear wave source is in a range between about 0.2 mm and about 8.0 cm.

30. A method according to claim 19 wherein the transmitting comprises transmitting ultrasound energy into tissue using a first modality; and wherein the tracking comprises tracking the movement of the offset tissue in response to the extended shear wave using a second modality.

31. A method according to claim 18 wherein transmitting comprises transmitting unfocused ultrasound energy into the tissue to provide the virtual extended shear wave source.

32. A method according to claim 18 wherein the virtual extended shear wave source further generates a second extended shear wave that propagates opposite the second direction.

33. A method according to claim 18 wherein the transmitted ultrasound energy causes the tissue along the first direction to displace in a range between about 0.1 $\mu$m and about 300 $\mu$m.

34. A system for imaging tissue using shear wave ultrasound, the system comprising:

means for tracking tissue to obtain first position data associated with tissue;

means for transmitting ultrasound energy into the tissue in a first direction to provide a virtual extended shear wave source that generates an extended shear wave that propagates in a second direction substantially orthogonal to the first direction to cause movement of tissue that is offset from the virtual extended shear wave source;

means for determining at least one imaging parameter based on at least the first position data; and means for generating image data associated with the tissue based on the at least one imaging parameter.

35. A computer program product for scanning tissue using ultrasound comprising a computer readable storage medium having computer-readable program code means embodied in said medium, said computer-readable program code means comprising:

computer-readable program code means for tracking tissue to obtain first position data associated with tissue;

computer-readable program code means for transmitting ultrasound energy into the tissue in a first direction to provide a virtual extended shear wave source that generates an extended shear wave that propagates in a second direction substantially orthogonal to the first direction to cause movement of tissue that is offset from the virtual extended shear wave source;

computer-readable program code means for determining at least one imaging parameter based on at least the first position data; and computer-readable program code means for generating image data associated with the tissue based on the at least one imaging parameter.

* * * * *

UNITED STATES PATENT AND TRADEMARK OFFICE
CERTIFICATE OF CORRECTION

PATENT NO. : 6,764,448 B2  
APPLICATION NO. : 10/266096  
DATED : July 20, 2004  
INVENTOR(S) : Trahey et al.

Page 1 of 1

It is certified that error appears in the above-identified patent and that said Letters Patent is hereby corrected as shown below:

In the Specification:

Column 1, line 9: delete "Grant No. RG-00-0272 from the Whitaker Foundation and"

Column 1, line 10: correct "and under Federal Grant No. 1R01CA92183-01 from the" to read
-- Federal Grant No. 1R01CA92183-01 awarded by the --

Column 9, Line 18: insert the following paragraph:
-- This invention was made with support under Grant No. RG-00-0272 from the Whitaker Foundation. --

Signed and Sealed this
Twenty-fifth Day of March, 2014

Michelle K. Lee
*Deputy Director of the United States Patent and Trademark Office*

UNITED STATES PATENT AND TRADEMARK OFFICE
CERTIFICATE OF CORRECTION

PATENT NO.         : 6,764,448 B2                                    Page 1 of 1
APPLICATION NO.    : 10/266096
DATED              : July 20, 2004
INVENTOR(S)        : Trahey et al.

It is certified that error appears in the above-identified patent and that said Letters Patent is hereby corrected as shown below:

In the Specification:

Column 1, line 9: delete "Grant No. RG-00-0272 from the Whitaker Foundation and"

Column 1, line 10: correct "and under Federal Grant No. 1R01CA92183-01 from the" to read
-- Federal Grant No. 1R01CA92183-01 awarded by the --

Column 1, line 11: please correct "National Institutes of Health, National Cancer Institute. The" to
read -- National Institutes of Health. The --

Column 9, Line 18: insert the following paragraph:
-- This invention was made with support under Grant No. RG-00-0272 from the
Whitaker Foundation. --

This certificate supersedes the Certificate of Correction issued March 25, 2014.

Signed and Sealed this
Eighth Day of July, 2014

Michelle K. Lee
*Deputy Director of the United States Patent and Trademark Office*